United States Patent [19]

Kandelman

[11] Patent Number: 5,395,241
[45] Date of Patent: Mar. 7, 1995

[54] SOLUTION OF STANNOUS AND AMINO FLUORIDES AND METHOD OF USE DENTAL TREATMENT

[76] Inventor: Daniel Kandelman, 7380 Maynard, Montreal, Quebec, Canada, H3R 3B4

[21] Appl. No.: 20,729

[22] Filed: Feb. 22, 1993

[30] Foreign Application Priority Data

Feb. 21, 1992 [FR] France .................................. 92 02134

[51] Int. Cl.$^6$ ................................................ A61C 5/00
[52] U.S. Cl. ................................. 433/217.1; 424/49; 424/52
[58] Field of Search ............... 433/215, 217.1; 424/49, 424/52, 54

[56] References Cited

U.S. PATENT DOCUMENTS

| | | | |
|---|---|---|---|
| 4,515,910 | 5/1985 | Rawls et al. | 523/115 |
| 4,533,544 | 8/1985 | Groat et al. | 424/52 |
| 5,057,310 | 10/1991 | Hill et al. | 424/49 |
| 5,160,737 | 11/1992 | Friedman et al. | 424/49 |
| 5,194,004 | 3/1993 | Bergersen | 433/215 |
| 5,252,577 | 10/1993 | Breuer et al. | 433/49 |

FOREIGN PATENT DOCUMENTS

91/07163 4/1991 WIPO .

OTHER PUBLICATIONS

The Effects of Desensitizing Agents on the Hydraulic Conductance of Human Dentin in vitro by Joel D. Greenhill and David H. Pashley (Departments of Endodontics, Oral Biology, and Physiology, Medical College of Georgia, School of Dentistry, Augusta, Ga., 30912, from Densensitizing Agents and Fluid Flow, vol. 60, No. 3, Mar. 1981.

The Effects of Two Fluoride Tooth Pastes on Dentinal Sensitivity (A Clinical Evaluation) by D. Kandleman, DMD, MPH; G. Gagnon, PhD; D. Ruel, DMD; D. Peters, DMD and Trépanier, DMD from Preventive Dentistry-vol. 78, No. 11, Nov. 1988.

A Review of Current Approaches to In-Office Management of Tooth Hypersensitivity by Henry O. Trowbridge, DDS, PhD and David R. Sivler, DMD (Clinical Characteristics of Dentinal Hypersensity) from Dental Clinics of North America-vol. 34, No. 3, Jul. 1990.

Patent Abstracts of Japan, vol. 14, No. 68, (C-686) [4011], Feb. 8, 1990.

Primary Examiner—John J. Wilson
Attorney, Agent, or Firm—Foley & Lardner

[57] ABSTRACT

The invention is concerned with a solution adherent on the surfaces of the teeth and intended for the treatment of tooth hypersensitivity, enhancement of tooth mineralization, and/or bacteriostatic or bactericidal treatment of the tooth surfaces, such a solution comprising the combination of:
   an amino fluoride;
   a stannous fluoride; and
   a biocompatible vehicle consisting of a natural resin and a solvent.

The invention is also concerned with a method of preparation of this solution and to its unique use.

15 Claims, No Drawings

SOLUTION OF STANNOUS AND AMINO FLUORIDES AND METHOD OF USE DENTAL TREATMENT

The present invention generally relates to the combined use of stannous and amino fluorides for the different dental treatment, such as the treatment of tooth hypersensitivity, the enhancement of tooth mineralization and/or the bactericidal action within the dental plate on the surface of the teeth.

It is known that fluoride ions have a desensitization action making them useful for decreasing tooth hypersensitivity the painful conditions of which are experienced when dentine becomes exposed either by loss of surface enamel (in the case of abrasion or erosion), or at the root neck near the enamel-dentine junction in the case of excessive tooth brushing, or by loss of protective cementum in gingival recession, or after periodontal surgery. The clinical symptoms of tooth hypersensitivity involve painful reactions to:

thermal stimuli (hot or cold);
tactile stimuli (hard instrument, nail's contact);
acidic or sweet foods.

The neural mechanisms of the tooth are presently not fully understood, but it seems obvious that the dentinal tubules that contain the dentinal nerve fibrils which transmit the various stimuli to the nervous system of the dental pulp, are subject to the same physical principles of fluid dynamics as observed in a capillary tube.

This means that a decrease in the diameter of the dentinal tubules can be created either by obstruction or obturation of the exposed tubules (GREENHILL J. D., PASHLEY D. H., *The effects of densitizing agents on the hydraulic conductance of human dentin in vitro*, J. Dent. Res. 1981: 60:686–698), the movement of fluids inside the dentinal tubules is reduced, thereby limiting the effective transmission of stimuli to the dental pulp.

A number of desensitizing agents have been tested for treatment of tooth hypersensitivity, which constitutes an important clinical problem. The tested therapeutic agents can be classified into four distinct groups, according to their mechanism of action, as follows:

precipitation of proteins;
obturation of dentinal tubules;
sealing of the orifice of exposed tubules; and
physical-chemical methods.

The fluoride ions are themselves classified in the second and fourth groups mentioned hereinabove, namely those that encompass the agents having a mechanism of action on the obturation of dentinal tubules and the physical-chemical methods which exploit the possibilities of electrical transport of the fluoride ions to the surface of the dentine.

At the present time, the mechanisms of action of fluoride in the treatment of tooth hypersensitivity are not clearly elucidated, but numerous clinical studies have emphasized the effectiveness of fluoride agents with respect to the problems of tooth hypersensitivity, and a number of laboratory studies have stated the following observations.

They ensure obturation of exposed dentinal tubules, and a reduction in fluid movement within the dentinal tubules.

The incorporation of fluoride within the dental tissues, favours the formation of a more highly calcified dentine and therefore more resistant to acid attack from the oral environment.

The use of sodium fluoride for the treatment of tooth hypersensitivity was first proposed by LUKOMSKY in 1941. Subsequent attempts have been carried out using various fluoride agents (particularly MFP) in different concentrations. In this regard, it is important here to specify that the evaluation of the effect of high concentrations of fluorides on the treatment of tooth hypersensitivity has been carried out using only fluoride agents like varnishes containing fluorides, or by regular professional application of fluoride gels or pastes. Accordingly, a study performed by this inventor on 121 adult patients having painful tooth hypersensitivity, demonstrated that after three weeks of using a highly concentrated fluoride toothpaste (3 g of sodium fluoride per 100 g of paste); the tactile sensitivity index indicated a 73% reduction for the test toothpaste vs. a 41% reduction for the placebo toothpaste. During the course of the study, the reaction time to thermal stimuli was increased by 214% for the experimental toothpaste and by only 32% for the placebo toothpaste (see KANDELMAN D., GAGNON G., RUEL D., PETERS D., TRÉPANIER J. —*Évaluation clinique de deux dentifrices aà haute teneur en fluor sur L'hypersensibiliteé dentineire*. L'information Dentaire, vol. 72, n° 38, p. 3609–3614, 1990; and KANDELMAN D. *Clinical evaluation of the effect of two fluoride tooth pastes on dentinal sensitivity*, Oral Health, vol. 78, No. 11, p. 63–65, 1988).

Furthermore, it is also known that fluoride has an important action on the process of mineralization.

In the presence of an incipient carious lesion (e.g.: chalky "white spots" of demineralization on the tooth crowns, or root cavities near the root neck) it is possible to observe in the presence of salivary fluoride, or fluoride directly in contact with the tooth surfaces in particular with dental plaque, a remineralization process characterized by depositing mineral substances in the previously demineralized sites. By this process, fluoride promotes the transformation of the initial hydroxyapatite crystals into more resistant fluoropatite crystals, to face the acid attack from the oral environment.

The slightly demineralized hard dental tissues are capable of absorbing greater quantities of fluoride than the normal adjacent hard surfaces. Therefore, these absorbent sites constitute fluoride reservoirs that will prolong the process of remineralization and increase the resistance of dental tissues on the demineralization sites. Numerous studies have demonstrated the importance of the concentration of fluoride in toothpastes on the effectiveness of their anticariogenic effect.

In addition, it is recognized that the presence of fluoride in toothpastes, topical fluoride gels or mouthwashes, can provide a bacteriostatic and/or bactericidal effect intraorally. At low concentrations of added fluoride in many toothpastes (1000 ppm), fluoride provides a bacteriostatic effect because it can reduce the metabolic activity of oral bacteria by inhibiting certain bacterial enzymes that participate in the process of sugar degradation. Toothpastes with higher concentrations of fluoride and/or topical fluoride gels however have a direct bactericidal effect.

The present invention is based upon the discovery that the incorporation of two known types of fluoride, namely amino fluoride (in all of its various organic forms) and stannous fluoride, formulated in a biocompatible natural resin vehicle, can produce a solution that adheres to the surface of teeth, that is particularly effective for the treatment of tooth hypersensitivity, the enhancement of the process of tooth mineralization, and/or bacteriostatic or bactericidal treatment of the teeth.

This solution by its composition, when properly applied to the tooth surfaces, can provide a physical-chemical sealing of the open orifices of the dentinal tubules, as well as prolonging the therapeutic action on the exposed sites.

It has also been discovered that the synergistic action of stannous fluoride and amino fluoride provides an important antibacterial action, probably equivalent to that of chlorhexidine, for a wide range of bacteria implicated in the mechanisms of cavities and periodontal diseases.

The main purpose of this invention is to provide an adherent solution on the surface of the teeth, used for the treatment of tooth hypersensitivity, the enhancement of the mineralization process, and/or the bacteriostatic or bactericidal treatment of oral surfaces (tooth and mucosal surfaces), characterized by the combination of:
- an amino fluoride;
- a stannous fluoride; and
- a biocompatible vehicle comprised of a natural resin and a solvent for the resin.

The purpose of the invention also provides a method of preparation for the adherent solution described hereinabove, characterized by:
- the preparation of solutions of stannous fluoride and amino fluoride;
- the preparation of the vehicle by adding the selected solvent to the natural resin; and
- the incorporation of the fluoride solutions in the prepared vehicle, to obtain the desired final composition.

A further purpose of the invention is a method of treatment of tooth hypersensitivity, of enhancement of the process of mineralization, and/or of bacteriostatic or bactericidal treatment of oral surfaces, characterized by:
- washing and drying the dental surfaces to be treated;
- applying a concentrated aqueous solution of stannous fluoride onto the dental surfaces;
- applying a concentrated solution of amino fluoride onto the same dental surfaces to be treated; and
- covering the surfaces on which the fluoride solutions are applied, with an adherent protective solution.

As previously indicated, the adherent solution according to this invention comprises three fundamental elements: the active ingredients constituted by the two fluorides, the vehicle, and the solvent.

The active ingredients are the two fluorides mentioned hereinabove. For amino fluoride, one can use commercial products sold under the commercial denominations 242,297 and/or 335 GABA Switzerland. For stannous fluoride, one can use those sold by PROFESSIONAL COMPOUNDING CENTER OF AMERICA, Houston, Tex.

The selected vehicle is preferably constituted of biocompatible natural resins, including in particular the entire group of resins soluble in ethanol like the natural resins derived from elemi oil, the copals of Manila and Congo, Damar Batu, and East Indies, Elemi, Sandarac Yacca, Mastic and Shellac.

The selected solvent must also be biocompatible. The suggested solvent of choice is ethanol.

All of the amino fluorides, with the exception of amino fluoride 242, are soluble, although solubility may occur very slowly. For these reasons, it may sometimes be useful to slightly heat the solution.

In ethyl alcohol, the amino fluorides 297 and 335 are soluble, whereas the amino fluoride 242 is solubilized in ethyl alcohol, only after heating to 60° C. The heating temperature of the amino fluoride solutions, and the consistency of the resultant solution obtained after cooling, depend upon the desired fluoride concentration.

As previously mentioned, the association of amino and stannous fluoride in a natural resin chemically and biologically compatible, has been shown to have an effective and extremely potent antibacterial action, against a wide spectrum of bacteria suspected in the mechanisms of cavities and periodontal diseases.

Each type of fluoride tested individually in numerous clinical trials, demonstrated a significant antibacterial action. However, the combination of the two different fluorides, amino and stannous together has created an important synergistic effect.

The use of a vehicle in the form of a natural resin as previously described, as a carrier for the two selected fluorides, provides the following advantages:
- adherence and preservation of a rapid dilution of the active ingredients due to the incorporation of the active ingredients in the natural resin;
- prolongation of the duration of the action of the active ingredients on the exposed sites, due to the adherence properties described hereinabove;
- excellent diffusion of the fluoride ions through the varnish of the salivary fluids to the dental surfaces; and
- possibility of placing the varnish on the dental surfaces, and/or in the gingiva-dental crevice, and thereby providing a direct and prolonged action with respect to the bacteria responsible firstly, for dental cavities and secondly, periodontal diseases.

Therefore, the adherent solution according to the invention, is particularly well suited for use:
- against tooth hypersensitivity;
- as an antibacterial agent with respect to dental cavities and periodontal diseases and/or as a remineralizing agent.

This provides a certain number of advantages over the other methods of application of therapeutic fluoride agents such as toothpastes, mouthwashes, or gels, notably the advantages of a prolongation of the duration of the action of the therapeutic agents, and the possibility of acting simultaneously on a plurality of specific sites and exposed to different problems, as for example, the presence of bacteria in dental plaque at the level of dental surfaces and/or the gingival crevice, the presence of demineralized white spots, or symptoms of painful tooth hypersensitivity.

The adherent solution according to the invention, also provides a certain number of advantages over the other solutions of other therapeutic agents in a varnish. Thus, it provides a possibility of multifactorial action (tooth hypersensitivity, antibacterial and remineralization) due to the association of the amino and stannous fluorides, incorporated into a natural resin varnish.

The invention and its method of use will be better understood by reading the non-limitative description of the following several methods of preparation and application, as follows:

FIRST METHOD OF PREPARATION AND APPLICATION a) Preparation

The adherent solution is prepared by dissolving a natural resin that serves as a vehicle, in ethanol in a ratio of weight/volume of 1–40% (weight of resin/resultant volume of ethanol mixture). The amino fluoride (242, 297 or 335, GABA Switzerland) and the stannous fluoride are then incorporated in this vehicle and they are dissolved in their respective proportions up to 30% weight/volume, at ambient temperature so as to obtain the required solution.

To facilitate the dissolution of amino fluoride, the resultant solution thus obtained at ambient temperature, can be heated to a temperature of 40°–60° C. in a closed vessel to prevent any evaporation and then cooled again to ambient temperature.

This heating procedure can produce a solubilization of the amino fluoride at appropriate concentrations corresponding to a supersaturation in amino fluoride. This maximizes therefore, the interesting properties resulting from the supersaturation of the amino fluoride obtained after heating the solution and letting it cool at the ambient temperature.

b) Application

Clinically, the dental surfaces that are to be treated must be very clean and dry before the application of the adhesive solution. This is then applied to the dental surfaces where it can adhere for a period of up to one week before being easily brushed off with a toothbrush. This application is characterized by a reduction of tooth hypersensitivity on the affected sites.

SECOND METHOD OF PREPARATION AND APPLICATION a) Preparation

Initially, a concentrated aqueous solution containing up to 30% weight/volume, of stannous fluoride, is prepared.

At ambient temperature, the stannous fluoride dissolves in water in quantities ranging between 0.001% to 30% weight/volume. By shaking the mixture, it is possible to quickly obtain a clear, colorless solution of stannous fluoride.

Then, an adherent solution is prepared, containing up to 30% weight/volume of amino fluoride, incorporated as necessary with heating in a closed vessel, at 40°–60° C., in a biocompatible vehicle preferably comprising a natural resin associated with a solvent. This second adherent solution may also contain stannous fluoride (this may be the adherent solution prepared according to the first method of preparation).

These two solutions are intended to be applied separately.

b) Application

In contrast to the first method of application, the two solutions previously prepared are applied separately.

The concentrated aqueous stannous fluoride solution is initially applied after having been prepared (the stannous fluoride being unstable in aqueous solution and can quickly loose its effectiveness), to the clean and dry, hypersensitive tooth surfaces. This first fluoride layer is dried. The adherent amino fluoride solution incorporated into a varnish is then applied, with or without the insoluble stannous fluoride, on the same dried surfaces and left in place under the same conditions as previously described.

It is absolutely essential for the teeth to be clean and dry, and that the stannous fluoride solution be applied first. In fact, if the adherent solution including a varnish is applied first, the stannous fluoride solution will not be able to contact the dental surfaces, and will not therefore have any effect.

THIRD METHOD OF PREPARATION AND APPLICATION a) Preparation

Initially a concentrated aqueous stannous fluoride solution is prepared, as previously described.

Then an aqueous or concentrated alcoholic amino fluoride solution is prepared, as needed with heating at 40°–60° C., in a closed vessel.

Finally, a solution of a biocompatible natural resin is prepared.

These three solutions are intended to be applied separately.

b) Application

The aqueous stannous fluoride solution is first applied on the dental surfaces followed by the amino fluoride solution dissolved in water or in ethanol at the ambient temperature or at higher temperatures (depending on the type of amino fluoride selected). Then the surfaces are covered with the resin solution, which then serves as a protective casing. In this case, the order in which the two fluoride solutions are applied, is not of great importance.

Up to the present time, stannous fluoride solutions used as desensitizing agents were made with soluble stannous fluoride in gels or toothpaste. Although, this form of stannous fluoride can be effective in obturating the dentinal tubules and therefore in treating hypersensitivity problems, the incorporation of stannous fluoride into an adherent solution for application to dental surfaces, as this invention proposes, demonstrates that the solubility of this type of fluoride in the solution in which it is incorporated, is not absolutely required in order to obtain an effective desensitization. In fact, on the chemical level, this desensitization can be obtained by the use of a vehicle containing microscopic insoluble stannous fluoride particles, especially when the stannous fluoride is combined with amino fluoride.

The insoluble stannous fluoride in suspension, with or without an additional quantity of amino fluoride, is clinically effective if the stannous fluoride solution that is formed, is first vigorously shaken and immediately applied on the exposed dental surfaces, imparting in this way the fine stannous fluoride particles directly onto the dental surfaces by the adherence of the solution. Subsequently, when the solvent, i.e. ethanol, progressively evaporates, it leaves an adherent film on the treated dental surfaces, comprising the resin, the stannous fluoride particles, and the amino fluoride solubilized within the vehicle.

The combination of two kinds of fluoride into one vehicle, in the form of an adherent solution as in the first method of preparation previously described, provides a prolonged therapeutic action of the two active ingredients, and constitutes an innovative improvement in the means of treatment over previously used methods of desensitization.

By contrast, in the second method of application described hereinabove comprising two steps, the stannous fluoride solubilized in an aqueous solution prepared just before use, may provide a more important desensitization effect when its application is followed closely by the application of a second layer comprising the adherent resin solution and the amino fluoride. This two-step technique which employs the therapeutic action of two kinds of fluoride, allows the concentrations of the fluorides and their respective properties to be maximized specifically at the level of the treated dental surfaces. In fact, the subsequent application of the amino fluoride salts in the adherent solution provides a prolonged desensitization effect by increasing the quantity of available fluoride at the level of the dental surfaces, and the duration of action of the application of the aqueous stannous fluoride solution, whose effectiveness would otherwise be rapidly dissipated without the assured protection of the second layer of adhesive resin solution.

CLINICAL TESTS

A short term clinical study was conducted on four patients in order to evaluate the desensitization effect of an adherent solution described in this invention.

a) Methodology

Four adult patients were selected because they were suffering from tooth hypersensitivity problems on several teeth throughout one or more of the sextants of the dental arches. The sensitive teeth were characterized by painful reactions to thermal or tactile stimuli.

b) Adherent solution used

The adherent solution used for this clinical study was the following:

| Active ingredients: | stannous fluoride |
| | amino fluoride (242 GABA Switzerland) |
| Solvent: | ethanol |
| Vehicle: | shellac resin |

A group of homologous teeth as compared to the tested teeth, received identical treatment with an adherent placebo solution, wherein the resin was of the same composition as that tested and solubilized in the same conditions, but with active ingredients. The thermal and tactile sensitivity measurements were made at the start of the trials (before application of any solutions) then at each week, for three weeks after the initial application.

RESULTS

For the four patients, a significant reduction in tooth hypersensitivity was demonstrated. The decrease in painful symptoms was characterized by a significant increase in the reaction time to thermal and tactile stimuli, in addition to the rapid and prolonged improvement during the duration of the test, of the tooth hypersensitivity phenomena like that reported by the participants in this study. The same tests will be repeated in six months in order to measure the residual effect of these varnishes for these participants.

The tested solution adhered well to the dental surfaces for a period of time of up to one week. It could have been reapplied as needed, using the same protocol to provide the required effects.

The study demonstrated that the adherent solution according to the invention, certainly provides a reduction in the phenomena of tooth hypersensitivity.

The first results seem equally promising, in view of the following:

the reduction on the exposed dental surfaces and/or in the gingival crevice, of cariogenic bacteria and of those responsible for periodontal diseases;

the enhancement of the process of mineralization and/or remineralization.

I claim:

1. Tooth-adherent solution intended for the treatment of dental hypersensitivity, the enhancement of the process or mineralization and/or the bacteriostatic or bactericidal treatment of teeth, characterized in that it comprises the combination of:

an amino fluoride;

a stannous fluoride; and a biocompatible vehicle composed of a natural resin and a solvent for said resin.

2. Solution according to claim 1, characterized in that the natural resin is selected from the group consisting of Elemi oil, Copals of Manilla and Congo, Damar Batu and East Indies, Sandarac, Yacca, Mastic and Shellac and in that the solvent is ethanol.

3. Solution according to claim 1, characterized in that the vehicle consists of from 1 to 40% by weight of resin per volume of solvent.

4. Solution according to any one of claims 1, characterized in that it comprises up to 30% by weight of amino and stannous fluoride.

5. Method of preparation of the solution according to claim 1, characterized in that:

solutions of amino fluoride and stannous fluoride are prepared;

the vehicle is prepared by addition of the selected solvent to the natural resin; and the so-prepared solutions are incorporated in the so-prepared vehicle to obtain the desired composition.

6. Method according to claim 5, characterized in that the stannous fluoride solution that is prepared is an aqueous solution containing up to 30% by weight of stannous fluoride per volume.

7. Method according to claim 5, in which:

the obtained composition is heated to a temperature of 40° to 60° C. in a closed vessel; and the so-heated composition is then allowed to cool to ambient temperature.

8. Method for treatment of dental hypersensitivity, enhancement of the process of mineralization, and/or the bacteriostatic or bactericidal treatment of the teeth, characterized in that:

the tooth surfaces to be treated are cleaned and dried;

a concentrated aqueous stannous fluoride solution is applied to the tooth surfaces;

a solution of amino fluoride is applied to the same tooth surfaces to be treated; and the surfaces to which the fluoride solutions were applied are covered with a protective adherent solution.

9. Method according to claim 8, characterized in that the adherent protective solution is a solution of a biocompatible natural resin, which is applied after application of said two fluoride solutions.

10. Method according to claim 8, characterized in that the concentrated amino fluoride solution and the adherent protective solution form together a single solution that is applied after application and drying of the aqueous stannous fluoride solution.

11. Method according to claim 10, characterized in that the adherent solution containing the amino fluoride contains a biocompatible vehicle consisting of a natural resin and a solvent for said resin.

12. Method according to claim 11, characterized in that the adherent solution containing the amino fluoride also contains stannous fluoride.

13. Method according to claim 12, characterized in that the applied adherent solution comprises the combination of:
- an amino fluoride;
- a stannous fluoride; and
- a biocompatible vehicle composed of a natural resin and a solvent for said resin.

14. Method according to claim 8, characterized in that the adherent solution of amino fluoride is a water- or ethanol- based solution and in that, after application of this adherent amino fluoride solution, a varnish of a natural resin is applied to cover both of said fluoride solutions.

15. Method according to any one of claim 8, characterized in that the aqueous stannous fluoride first applied, contains up to 30% by weight of stannous fluoride per volume.

* * * * *